(12) United States Patent
Yoshida et al.

(10) Patent No.: US 10,743,769 B2
(45) Date of Patent: Aug. 18, 2020

(54) SKIN EVALUATION APPARATUS, SKIN EVALUATION METHOD, AND SKIN EVALUATION PROGRAM

(71) Applicant: FUJIFILM Corporation, Tokyo (JP)

(72) Inventors: Naoko Yoshida, Kanagawa (JP); Yoshitaka Yamaguchi, Kanagawa (JP); Hideyasu Ishibashi, Kanagawa (JP); Eriko Ikeda, Kanagawa (JP); Takeharu Tani, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 353 days.

(21) Appl. No.: 15/709,517

(22) Filed: Sep. 20, 2017

(65) Prior Publication Data

US 2018/0000349 A1    Jan. 4, 2018

Related U.S. Application Data

(63) Continuation of application No. PCT/JP2016/054775, filed on Feb. 19, 2016.

(30) Foreign Application Priority Data

Mar. 31, 2015   (JP) .................. 2015-070855

(51) Int. Cl.
*A61B 5/00*    (2006.01)
*A61B 5/107*    (2006.01)

(52) U.S. Cl.
CPC ............ *A61B 5/0077* (2013.01); *A61B 5/107* (2013.01); *A61B 5/1079* (2013.01); *A61B 5/442* (2013.01);

(Continued)

(58) Field of Classification Search
CPC ..... A61B 5/0077; A61B 5/1079; A61B 5/442; A61B 5/742; A61B 5/443; A61B 5/107; A61B 2576/02
See application file for complete search history.

(56) References Cited

U.S. PATENT DOCUMENTS 4,423,736 A * 1/1984 DeWitt ................ A61B 5/0059
 600/306
2004/0218810 A1* 11/2004 Momma .............. A61B 5/0064
 382/162

(Continued)

FOREIGN PATENT DOCUMENTS

JP         09042944 A  *  2/1997
JP         2003-190120 A    7/2003

(Continued)

OTHER PUBLICATIONS

Yoshida, Kenichiro, et al. "Relationship between microstructure of the skin surface and surface reflection based on geometric optics." Journal of dermatological science 66.3 (2012): 225-232. (Year: 2012).*

(Continued)

*Primary Examiner* — Pascal M Bui Pho
*Assistant Examiner* — Sean D Mattson
(74) *Attorney, Agent, or Firm* — Sughrue Mion, PLLC

(57) ABSTRACT

A skin evaluation apparatus includes a shape information acquisition unit 22 that acquires information on a surface unevenness shape of the skin; an optical feature information acquisition unit 23 that acquires information on an optical feature of the skin; and an evaluation unit 24 that evaluates gloss of the skin on the basis of the information on the surface unevenness shape and the information on the optical feature.

8 Claims, 2 Drawing Sheets

(52) U.S. Cl.
CPC ............. *A61B 5/443* (2013.01); *A61B 5/742* (2013.01); *A61B 2576/02* (2013.01)

(56) References Cited

U.S. PATENT DOCUMENTS

| | | | |
|---|---|---|---|
| 2007/0092160 A1 | 4/2007 | Fujii et al. | |
| 2009/0054744 A1* | 2/2009 | Kitamura | A61B 5/0082 600/306 |
| 2014/0350395 A1* | 11/2014 | Shachaf | G06T 7/0012 600/431 |
| 2015/0230712 A1* | 8/2015 | Aarabi | A61B 5/0077 600/476 |
| 2016/0035109 A1 | 2/2016 | Kikuchi et al. | |
| 2017/0119301 A1* | 5/2017 | Kimura | G06T 7/0012 |

FOREIGN PATENT DOCUMENTS

| | | |
|---|---|---|
| JP | 2004-166801 A | 6/2004 |
| JP | 2005-429 A | 1/2005 |
| JP | 4133248 B2 | 8/2008 |
| JP | 5085344 B2 | 11/2012 |
| JP | 5340907 B2 | 11/2013 |
| JP | 2014213065 A | 11/2014 |
| WO | 2016/158061 A1 | 10/2016 |

OTHER PUBLICATIONS

International Preliminary Report on Patentability issued from the International Bureau in counterpart International Application No. PCT/JP2016/054775, dated Oct. 3, 2017.
Translation of Written Opinion dated May 17, 2016, issued by the International Bureau in counterpart Application No. PCT/JP2016/054775.
International Search Report for PCT/JP2016/054775 dated May 17, 2016 issued by the International Bureau in counterpart Application No. PCT/JP2016/054775.
Communication dated Dec. 19, 2017 from the Japanese Patent Office in counterpart Application No. 2015-070855.

* cited by examiner

SKIN EVALUATION APPARATUS, SKIN EVALUATION METHOD, AND SKIN EVALUATION PROGRAM

CROSS-REFERENCE TO RELATED APPLICATIONS

This application is a Continuation of PCT International Application No. PCT/JP2016/054775 filed on Feb. 19, 2016, which claims priority under 35 U.S.C. § 119(a) to Japanese Patent Application No. 2015-070855 filed on Mar. 31, 2015. Each of the above application(s) is hereby expressly incorporated by reference, in its entirety, into the present application.

BACKGROUND OF THE INVENTION

1. Field of the Invention

The present invention relates to a skin evaluation apparatus, a skin evaluation method, and a non-transitory computer readable recording medium storing a skin evaluation program for evaluating gloss of the skin.

2. Description of the Related Art

"Transparency", "elasticity", "moistness", "gloss", and the like are used as conditions of a beautiful skin. Here, it is considered that gloss of the skin is an important factor since people feel moist, feel elastic, or feel youthful in a case where the gloss of the skin exists.

Accordingly, in evaluation of a skin state or in product design of cosmetics, drugs, or the like used for the skin, it is important to quantitatively evaluate gloss of the skin.

As a general method for quantitatively evaluating gloss of the skin, there is a method for acquiring two images of a non-polarized image and a polarized image (crossed nicols), generating a specular reflection image from a differential image of the two images, and evaluating gloss by a brightness value or a brightness distribution of the specular reflection image.

JP4133248B discloses a method for extracting specular reflection components from an image of the skin, acquiring a physical glossiness from a mean value of brightnesses of a specular reflection image, calculating a asperity of appearance by a mean square value of frequency components indicating a texture of the skin by multiple resolution analysis of the specular reflection components, and evaluating gloss on the basis of the asperity of the appearance and the glossiness.

In addition, JP5340907B discloses a method for acquiring two images of a non-polarized image and a polarized image (crossed Nichol prism), correcting brightness levels of the images, generating a differential image of B channel images of the two images, calculating a mean and a peeling degree of a normal distribution of the differential image, and evaluating gloss and smoothness of the skin on the basis of the peeling degree.

Further, JP5085344B discloses a method for evaluating the gloss of hair. Specifically, JP5085344B discloses a method for evaluating the gloss of hair on the basis of a result obtained by imaging the hair and fractal-analyzing a hair region.

Furthermore, JP2003-190120A discloses a method for calculating a correspondence relationship between an optical feature value of the skin and a sensitivity evaluation score in advance, and evaluating the appearance of skin on the basis of an optical measurement value of the skin which is an evaluation target and the correspondence relationship.

SUMMARY OF THE INVENTION

Here, the gloss of the skin is changed according to light scattering within the skin in addition to specular reflection and diffuse reflection on the basis of reflection of a skin surface. Accordingly, in a case where gloss of the skin is evaluated, it is preferable to consider both of a physical feature of the skin and an optical feature of the skin. The above-mentioned JP4133248B, JP5340907B, JP5085344B, and JP2003-190120A do not propose a method for considering both of the physical feature of the skin and the optical feature of the skin.

In consideration of the above-mentioned problems, an object of the invention is to provide a skin evaluation apparatus, a skin evaluation method, and a non-transitory computer readable recording medium storing a skin evaluation program capable of evaluating gloss of the skin in consideration of both of a physical feature of the skin and an optical feature of the skin to quantitatively evaluate gloss of the skin closer to a practical point of view.

According to an aspect of the invention, there is provided a skin evaluation apparatus comprising: a shape information acquisition unit that acquires information on a surface unevenness shape of skin; an optical feature information acquisition unit that acquires information on an optical feature of the skin; and an evaluation unit that evaluates gloss of the skin on the basis of the information on the surface unevenness shape and the information on the optical feature.

In the above-described skin evaluation apparatus according to this aspect of the invention, the shape information acquisition unit may acquire an image obtained by imaging the skin, and acquires the information on the surface unevenness shape on the basis of the acquired image.

In the above-described skin evaluation apparatus according to this aspect of the invention, the shape information acquisition unit may acquire an image obtained by imaging peeling of stratum corneum taken from the skin, and acquires the information on the surface unevenness shape on the basis of the acquired image.

In the above-described skin evaluation apparatus according to this aspect of the invention, the shape information acquisition unit may read and acquire the information on the surface unevenness shape of the skin which is stored in advance in a data server apparatus.

In the above-described skin evaluation apparatus according to this aspect of the invention, the shape information acquisition unit may acquire information indicating a state of the stratum corneum of the skin as the information on the surface unevenness shape.

In the above-described skin evaluation apparatus according to this aspect of the invention, the shape information acquisition unit may acquire information on at least one of a width, a tilt angle, or a density of sulci cutis of the skin as the information on the surface unevenness shape.

In the above-described skin evaluation apparatus according to this aspect of the invention, the optical feature information acquisition unit may acquire a scattering coefficient within the skin as the information on the optical feature.

In the above-described skin evaluation apparatus according to this aspect of the invention, the optical feature information acquisition unit may acquire a slit optical image captured by irradiating the skin with slit light, and may acquire the scattering coefficient within the skin on the basis of the slit optical image.

In the above-described skin evaluation apparatus according to this aspect of the invention, the shape information acquisition unit may acquire information indicating the state of the stratum corneum of the skin and the information on the width, the tilt angle, and the density of the sulci cutis of the skin as the information on the surface unevenness shape, the optical feature information acquisition unit may acquire the scattering coefficient within the skin as the information on the optical feature, and the evaluation unit may evaluate the gloss of the skin on the basis of the information indicating the state of the stratum corneum of the skin and the information on the width, the tilt angle and the density of the sulci cutis of the skin, and the scattering coefficient within the skin.

In the above-described skin evaluation apparatus according to this aspect of the invention, the evaluation unit may evaluate that the gloss of the skin is good in a case where an area ratio of a peeling portion of the stratum corneum is 20% or less, the width of the sulci cutis of the skin is 50±30 µm, the tilt angle of the sulci cutis is 80 degrees or greater and 90 degrees or smaller, and the density of the sulci cutis is 30% or greater.

According to another aspect of the invention, there is provided a skin evaluation method comprising: acquiring information on a surface unevenness shape of skin; acquiring information on an optical feature of the skin; and evaluating gloss of the skin on the basis of the information on the surface unevenness shape and the information on the optical feature.

According to still another aspect of the invention, there is provided a non-transitory computer readable recording medium storing a skin evaluation program that causes a computer to function as: a shape information acquisition unit that acquires information on a surface unevenness shape of skin; an optical feature information acquisition unit that acquires information on an optical feature of the skin; and an evaluation unit that evaluates gloss of the skin on the basis of the information on the surface unevenness shape and the optical feature.

According to the skin evaluation apparatus, the skin evaluation method, and the non-transitory computer readable recording medium storing the skin evaluation program of the invention, the information on the surface unevenness shape of the skin is acquired, the information on the optical feature of the skin is acquired, and the gloss of the skin is evaluated on the basis of the information on the surface unevenness shape and the information on the optical feature. Accordingly, since the gloss of the skin is evaluated in consideration of both of a physical feature and an optical feature of the skin, it is possible to quantitatively evaluate gloss of the skin closer to a practical point of view.

DESCRIPTION OF THE PREFERRED EMBODIMENTS

Figure 1:
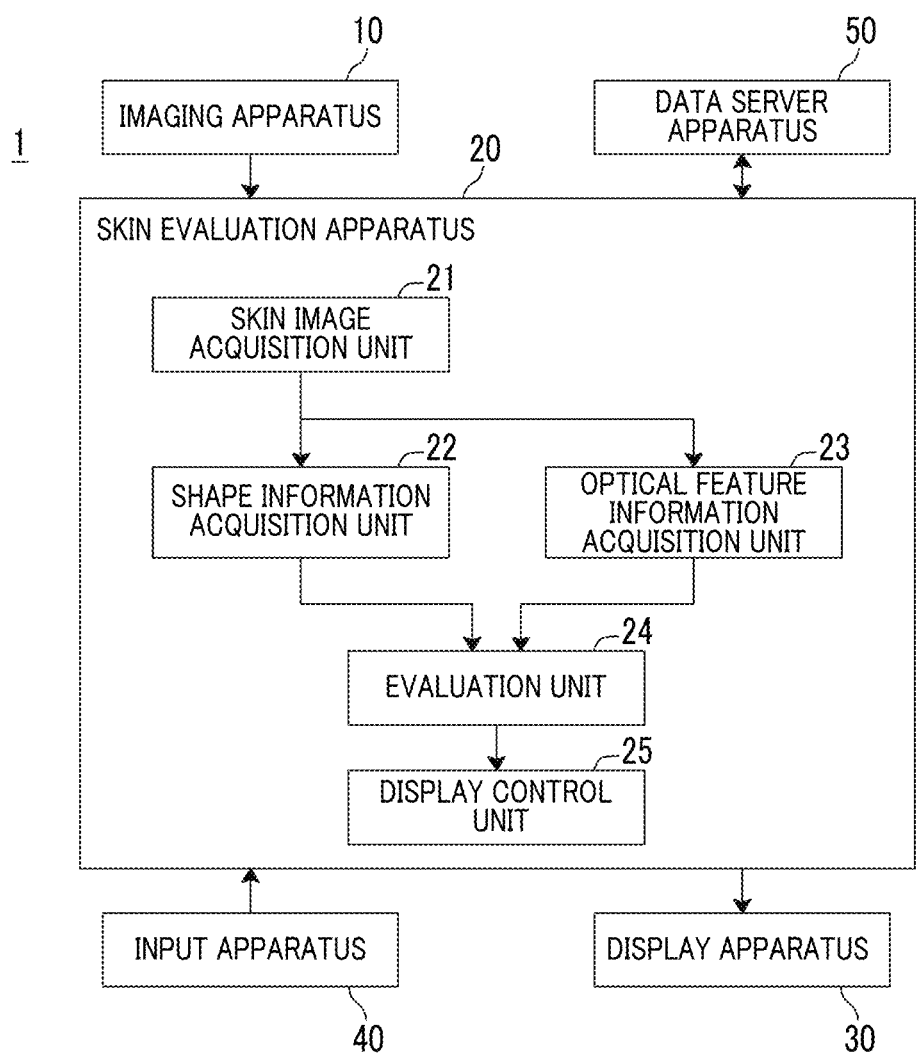
FIG. 1 is a block diagram showing a schematic configuration of a skin evaluation system using one embodiment of a skin evaluation apparatus of the invention.

Hereinafter, a skin evaluation system using an embodiment of a skin evaluation apparatus, a skin evaluation method, and non-transitory computer readable recording medium storing a skin evaluation program of the invention will be specifically described with reference to the accompanying drawings. FIG. 1 is a block diagram showing a schematic configuration of a skin evaluation system 1 of the embodiment. A configuration of a skin evaluation apparatus 20 shown in FIG. 1 is realized by installing an embodiment of a skin evaluation program of the invention on a computer and allowing the computer to execute the skin evaluation program. The skin evaluation program installed on the computer may be stored in a recording medium such as a compact disc-read only memory (CD-ROM), or may be distributed through a network such as the Internet.

The skin evaluation system 1 of this embodiment includes an imaging apparatus 10, a skin evaluation apparatus 20, a display apparatus 30, an input apparatus 40, and a data server apparatus 50, as shown in FIG. 1.

The imaging apparatus 10 includes a microscope that captures an image of the surface of the skin. The imaging apparatus 10 is configured to be able to image the surface of the skin at a magnification of 30 to 200 times. In this embodiment, information on a surface unevenness shape of a micro-order of peeling or the like of stratum corneum of the skin and information on a surface unevenness shape of a macro-order of sulci cutis or the like of the skin are acquired by a shape information acquisition unit 22 of the skin evaluation apparatus 20 (to be described later). Accordingly, in capturing an image for acquiring the information on the surface unevenness shape of the micro-order, the imaging apparatus 10 performs imaging at a magnification of 30 to 200 times, for example, and in capturing an image for acquiring the information on the surface unevenness shape of the macro-order, the imaging apparatus 10 performs imaging at a magnification of 30 to 50 times, for example. That is, it is preferable that the magnification in capturing the image for acquiring the information on the surface unevenness shape of the micro-order is equal to or greater than the magnification in capturing the image for acquiring the information on the surface unevenness shape of the macro-order.

The skin evaluation apparatus 20 includes a skin image acquisition unit 21, the shape information acquisition unit 22, an optical feature information acquisition unit 23, an evaluation unit 24, and a display control unit 25.

The skin image acquisition unit 21 acquires an image of the surface of the skin captured by the imaging apparatus 10. Specifically, as the image for acquiring the information on the surface unevenness shape of the micro-order as described above, for example, an image obtained by imaging the surface of the skin at a magnification of 30 to 200 times is acquired, and as the image for acquiring the information on the surface unevenness shape of the macro-order, for example, an image obtained by imaging the surface of the skin at a magnification of 30 to 50 times is acquired.

Further, the skin image acquisition unit 21 acquires an image for acquiring information on an optical feature of the skin by the optical feature information acquisition unit 23, and specifically, acquires a slit optical image captured by irradiating the skin with slit light. The slit optical image may be captured by the imaging apparatus 10 in a state where a light source unit that irradiates the imaging apparatus 10 with slit light is provided, for example, or may be captured by an apparatus that is provided separately from the imaging apparatus 10.

The shape information acquisition unit 22 acquires information on a surface unevenness shape of a micro-order of the surface of the skin and information on a surface unevenness shape of a macro-order thereof on the basis of an image of the surface of the skin acquired by the skin image acquisition unit 21.

The shape information acquisition unit 22 acquires information indicating the state of stratum corneum of the skin as the information on the surface unevenness shape of the micro-order, and in this embodiment, acquires information on peeling of the stratum corneum. Dry skin has a lot of peeling of the stratum corneum compared with moist skin, and is whitish with no gloss. Accordingly, a peeling state of the stratum corneum of the skin is used as one index for evaluating gloss of the skin.

Specifically, the shape information acquisition unit 22 performs a gray conversion process with respect to an image obtained by imaging the surface of the skin at a magnification of 30 to 200 times to form a brightness image. Further, the shape information acquisition unit 22 extracts a white portion in which a brightness value is equal to or greater than a predetermined threshold value as a portion in which stratum corneum is peeled, and acquires the area of the white portion or an area ratio of the white portion to the entire image as information indicating the state of the stratum corneum of the skin.

In this embodiment, the area of the white portion in the brightness image or the area ratio thereof is acquired as described above, but the invention is not limited thereto. For example, edges in a brightness image may be detected to acquire the number of the edges. Further, in order to extract a white portion in the brightness image or the edges with high accuracy, a contrast emphasis process, a frequency emphasis process, or the like may be performed with respect to the brightness image.

The area ratio of the portion in which the stratum corneum is peeled may be calculated by tape stripping. In this case, a tape is pushed against the skin and then is peeled, the peeled tape is stained to easily recognize peeled corneum. Further, the peeled corneum is observed at a magnification of 200 times using an optical microscope or the like, and the result is stored as image data. Then, a multi-layer region of the stratum corneum is extracted from the acquired image data, and then, it is possible to calculate the area ratio of the extracted multi-layer region. The extraction of the multi-layer region is performed by extracting a portion with a high density compared with that of a stratum corneum single-layer portion, with reference to the density or a brightness distribution of a stained image. Alternatively, a portion in which the brightness becomes lower may be extracted as the multi-layer region.

Figure 2:
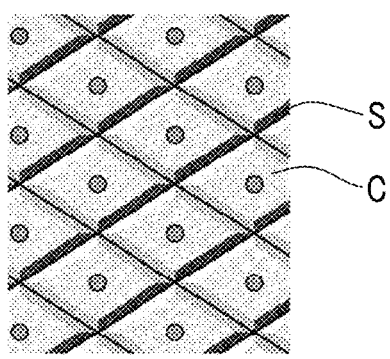
FIG. 2 is a schematic view of sulci cutis and crista cutis.
Figure 3:
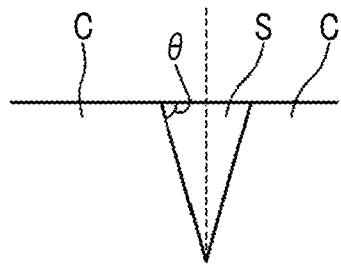
FIG. 3 is a schematic view illustrating a tilt angle of sulci cutis.

Further, the shape information acquisition unit 22 acquires information indicating the state of sulci cutis of the skin as the information on the surface unevenness shape of the macro-order. Specifically, the shape information acquisition unit 22 of the embodiment acquires information on the width of sulci cutis of the skin, a tilt angle of the sulci cutis, and the density of the sulci cutis. On the surface of the skin, sulci cutis formed by fine grooves and crista cutis surrounded by the sulci cutis are present, and states of the sulci cutis and the crista cutis are indicated as so-called skin textures. FIG. 2 schematically shows sulci cutis S and crista cutis C of the skin. Further, FIG. 3 is a diagram showing a cross-sectional view of the skin in a depth direction, in which a tilt angle of sulci cutis S is a tilt angle θ shown in FIG. 3.

Dry skin has sulci cutis having a width larger than that of moist skin. Further, dry skin has sulci cutis having a tilt angle smaller than that of moist skin. In addition, dry skin has sulci cutis having a low and sparse density compared with that of moist skin.

Accordingly, in this embodiment, information on the width of the sulci cutis of the skin, the tilt angle of the sulci cutis, and the density of the sulci cutis are used as indexes for the evaluation of gloss of the skin. In this embodiment, by using three types of information of the width of the sulci cutis of the skin, the tilt angle of the sulci cutis, and the density of the sulci cutis, the accuracy of evaluation of gloss of the skin is enhanced, but at least one type of information among the three types of information may be used. Further, since the tilt angle of the sulci cutis is derived from the width of the sulci cutis and the depth of the sulci cutis, information on the width of the sulci cutis and the depth of the sulci cutis may be used.

Specifically, the shape information acquisition unit 22 performs a gray conversion process with respect to an image obtained by imaging the surface of the skin at a magnification of 30 to 50 times to form a brightness image, and extracts portions of sulci cutis from the brightness image. As a method for extracting the portions of the sulci cutis, for example, since the portions of the sulci cutis become an image darker than peripheral portions, portions in which the brightness value is equal to or greater than a predetermined threshold value may be extracted as the portions of the sulci cutis. Further, the portions of the sulci cutis may be extracted using a straight line matching method, may be extracted using a Fast Fourier Transform (FFT) frequency filter, or may be extracted by applying an anisotropy filter such as a difference of Gaussian (DOG) filter. In extracting the portions of the sulci cutis, in order to extract the portions of the sulci cutis in the brightness image with high accuracy, a contrast emphasis process, a frequency emphasis process, or the like may be performed with respect to the brightness image.

Further, the shape information acquisition unit 22 calculates the ratio of the area of the portions of the sulci cutis to the area of the entire brightness image to acquire information on the density of the sulci cutis. Further, the shape information acquisition unit 22 sets a perpendicular line in a direction orthogonal to a stretch direction of the extracted portion of each sulci cutis and acquires a length between intersections of contour lines of the portion of the sulci cutis and the perpendicular line as information on the width of the sulci cutis. Specifically, an arbitrary part among the plural extracted portions of the sulci cutis is cut into N pieces, a perpendicular line is set with respect to the cut portion of each sulci cutis, and thus, the width of the sulci cutis is calculated. Here, a straight line may be radially set from the center of the brightness image, sulci cutis that crosses perpendicularly to the straight line may be specified, and a length between intersections of contour lines of a portion of the sulci cutis and the straight line may be calculated as the width of the sulci cutis. Alternatively, perpendicular lines may be set with respect to plural locations of a portion of one sulci cutis to calculate a mean value of calculated widths of the sulci cutis. Furthermore, the number of perpendicular lines set with respect to one direction of sulci cutis may be set in advance, and positions thereof may be randomly set, so that the width of the sulci cutis may be calculated.

Further, the shape information acquisition unit 22 divides the width of the sulci cutis obtained as described above by a minimum brightness value of the portion of the sulci cutis to acquire information on a tilt angle of the sulci cutis. The minimum brightness value of the portion of the sulci cutis represents a minimum brightness value among brightness values on the perpendicular line set in acquiring the information on the width of the sulci cutis. The minimum brightness value of the portion of the sulci cutis is a brightness value of a darkest portion of the sulci cutis, that is, represents the depth of the sulci cutis. Accordingly, the division of the width of the sulci cutis by the minimum brightness value corresponds to division of the width of the sulci cutis by the depth of the sulci cutis, that is, corresponds to acquisition of information on the tilt angle θ shown in FIG. 3.

The depth of the sulci cutis may be estimated on the basis of the minimum brightness value of the portion of the sulci cutis, and the width of the sulci cutis may be divided by the depth, so that the information on the tilt angle may be acquired. With respect to estimation of the depth on the basis of the minimum brightness value, for example, a table in which the minimum brightness value and the depth are associated with each other may be used.

Returning to FIG. 1, the optical feature information acquisition unit 23 acquires information on an optical feature of the skin. Specifically, the optical feature information acquisition unit 23 of this embodiment acquires a scattering coefficient within the skin as information on the optical feature of the skin. Dry skin has a scattering coefficient larger than that of moist skin. Accordingly, in this embodiment, the scattering coefficient within the skin is used as an index for evaluating gloss of the skin.

The optical feature information acquisition unit 23 acquires a slit optical image acquired by the skin image acquisition unit 21, and calculates the scattering coefficient within the skin on the basis of the slit optical image. Specifically, the optical feature information acquisition unit 23 performs a gray conversion process for each of a red (R) component, a green (G) component, and a blue (B) component with respect to the slit optical image to form a brightness image. Further, the optical feature information acquisition unit 23 one-dimensionally converts the brightness image for each of the R, G. and B components to calculate a brightness profile. Then, the optical feature information acquisition unit 23 causes the brightness profile to be fitted to a dipole approximation to calculate a scattering coefficient. Since the calculation of the scattering coefficient on the basis of the slit optical image is already a known method, detailed description thereof is omitted.

The evaluation unit 24 evaluates gloss of the skin on the basis of the information on the surface unevenness shape of the skin acquired by the shape information acquisition unit 22 and the information on the optical feature of the skin acquired by the optical feature information acquisition unit 23. Specifically, the evaluation unit 24 of this embodiment evaluates gloss of the skin on the basis of five parameters of information indicating a peeling state of stratum corneum of the skin, information on the width of sulci cutis of the skin, a tilt angle of the sulci cutis, and the density of the sulci cutis, and a scattering coefficient within the skin.

As a method for evaluating gloss of the skin, specifically, there is a method for evaluating that the gloss of the skin is good in a case where an area ratio of a portion in which stratum corneum is peeled (white portion) is equal to or smaller than a threshold value of a predetermined area, the width of sulci cutis of the skin is within a threshold value range of a predetermined sulci cutis width, a tilt angle of the sulci cutis of the skin is within a predetermined tilt angle threshold value range, the density of the sulci cutis is equal to or greater than a predetermined density threshold value, and a scattering coefficient is within a predetermined scattering coefficient threshold value range.

As specific numerical values, it is evaluated that gloss of the skin is good in a case where the area ratio of the portion in which the stratum corneum is peeled (white portion) is equal to or smaller than 20%, the width of the sulci cutis of the skin is within 50±30 μm, the tilt angle of the sulci cutis of the skin is 80 degrees or greater and 90 degrees or less, the density of the sulci cutis is equal to or greater than 30%, and the scattering coefficient is 10 $mm^{-1}$ to 25 $mm^{-1}$ (a wavelength of light is 577 nm) The threshold value conditions are values confirmed by experiments in advance.

Specifically, in a case where the skin is imaged using a microscope to calculate the area ratio of the portion in which the stratum corneum is peeled, the surface of the skin is imaged at a magnification of 200 times, and a gray conversion process is performed with respect to the captured image to binarize the image using a predetermined threshold value. Then, the area of the peeled stratum corneum portion is calculated, and is divided by the resolution of the captured image to calculate the area ratio of the portion in which the stratum corneum is peeled.

Further, with respect to the width of the sulci cutis of the skin, the surface of the skin is imaged at a magnification of 50 times, and a gray conversion process is performed with respect to the captured image to form a brightness image, and a portion of sulci cutis is extracted from the brightness image. In addition, an arbitrary part among the plural extracted portions of the sulci cutis is randomly cut into N pieces, and a perpendicular line is set with respect to the cut portion of the sulci cutis, so that the width of the sulci cutis is calculated.

Furthermore, the evaluation unit 24 evaluates, in a case where a numerical value of at least one parameter among the above-mentioned five parameters does not satisfy a threshold condition, gloss of the skin in stages according to the number of parameters that do not satisfy the threshold condition. For example, in a case where one parameter among the five above-mentioned parameters does not satisfy the threshold value condition, the evaluation unit 24 sets an evaluation value of the gloss to 4, in a case Where two parameters among the five above-mentioned parameters do not satisfy the threshold value condition, the evaluation unit 24 sets an evaluation value of the gloss to 3, in a case where three parameters among the five above-mentioned parameters do not satisfy the threshold condition, the evaluation unit 24 sets an evaluation value of the gloss to 2, and in a case where four parameters among the five above-mentioned parameters do not satisfy the threshold value condition, the evaluation unit 24 sets an evaluation value of the gloss to 1. In this way, the evaluation unit 24 sets the respective evaluation values as evaluation results.

The display control unit 25 displays the evaluation results in the evaluation unit 24 on the display apparatus 30. Further, the display control unit 25 displays images of the surface of the skin acquired by the skin image acquisition unit 21 on the display apparatus 30.

The display apparatus 30 is provided with a monitor such as a liquid crystal display. The display apparatus 30 may be a tablet terminal monitor. That is, a skin evaluation program may be installed on a tablet terminal to evaluate gloss of the skin, and an evaluation result thereof may be displayed thereon.

The input apparatus 40 is provided with a keyboard and a mouse, and receives a variety of setting inputs from a user. Further, a touch panel of the above-mentioned tablet terminal may serve as both of the display apparatus 30 and the input apparatus 40.

In this embodiment, information on a surface unevenness shape of the skin is acquired from an image of the surface of the skin, but a user may set and input the information on the surface unevenness shape of the skin using the input apparatus 40. Further, the user may set and input the information on the optical feature of the skin using the input apparatus 40.

Figure 4:
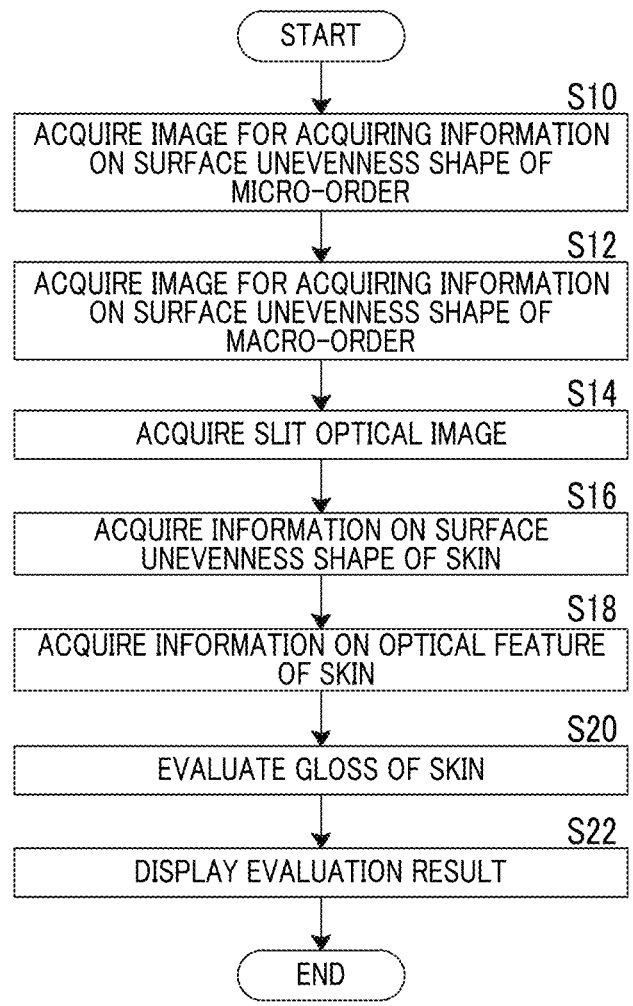
FIG. 4 is a flowchart illustrating an operation of the skin evaluation system using one embodiment of the skin evaluation apparatus of the invention.

Next, an operation of the skin evaluation system 1 according to this embodiment will be described with reference to a flowchart shown in FIG. 4.

First, an image of the surface of the skin for acquiring information on a surface unevenness shape of a micro-order and an image of the surface of the skin for acquiring information on a surface unevenness shape of a macro-order are captured using the imaging apparatus 10, and are acquired by the skin image acquisition unit 21 (S10 and S12). Further, capturing of a slit optical image as described above is performed, and is acquired by the skin image acquisition unit 21 (S14).

The images of the surface of the skin are input to the shape information acquisition unit 22 and the shape information acquisition unit 22 acquires information on a surface unevenness shape of the skin on the basis of the input images of the surface of the skin (S16). Specifically, the shape information acquisition unit 22 of this embodiment acquires information on a peeling state of stratum corneum of the skin, and information on the width, a tilt angle, and the density of sulci cutis.

Further, the slit optical image is input to the optical feature information acquisition unit 23, and the optical feature information acquisition unit 23 acquires information on an optical feature of the skin on the basis of the input slit optical image (S18). Specifically, the optical feature information acquisition unit 23 of this embodiment acquires a scattering coefficient within the skin.

The information on the peeling state of the stratum corneum of the skin and the information on the width, the tilt angle, and the density of the sulci cutis, acquired by the shape information acquisition unit 22, are input to the evaluation unit 24, and the scattering coefficient within the skin acquired by the optical feature information acquisition unit 23 is input to the evaluation unit 24. The evaluation unit 24 evaluates gloss of the skin on the basis of the information on the peeling state of the stratum corneum of the skin, the information on the width, the tilt angle, and the density of the sulci cutis, and the scattering coefficient within the skin (S20).

The evaluation result of the gloss of the skin in the evaluation unit 24 is input to the display control unit 25, and the display control unit 25 displays the input evaluation result on the display apparatus 30. Specifically, for example, a message or a mark indicating that the gloss of the skin is good, or an evaluation value of the gloss of the skin is displayed on the display apparatus 30.

According to the skin evaluation system 1 of the above-described embodiment, information on a surface unevenness shape of the skin is acquired, information on an optical feature of the skin is acquired, and gloss of the skin is evaluated on the basis of the information on the surface unevenness shape and the information on the optical feature. Accordingly, since the gloss of the skin is evaluated in consideration of both of a physical feature of the skin and an optical feature thereof, it is possible to quantitatively evaluate gloss of the skin closer to a practical point of view.

In the above-described embodiment, the shape information acquisition unit 22 acquires information on a surface unevenness shape on the basis of an image of the surface of the skin captured by the microscope, but the invention is not limited thereto. For example, a configuration in which the skin is cut, a sectional image of the skin is acquired using a scanning electron microscope (SEM), and information on a peeling state of stratum corneum is acquired on the basis of the sectional image may be used. The information on the peeling state of the stratum corneum may be acquired by analyzing a cross-sectional image in a similar way to the above-described embodiment, or a user may observe the cross-sectional image and may set and input the information on the peeling state of stratum corneum using the input apparatus 40.

Further, a configuration in which information indicating a peeling state of stratum corneum is stored in the data server apparatus 50 shown in FIG. 1 and the shape information acquisition unit 22 reads and acquires the information indicating the peeling state of the stratum corneum from the data server apparatus 50 on the basis of input predetermined information may be used. Specifically, for example, a table in which information on a peeling state of stratum corneum and the amount of moisture of the skin are associated with each other may be stored in the data server apparatus 50 in advance and the shape information acquisition unit 22 may acquire the information on the peeling state of the stratum corneum with reference to the table on the basis of the information on the input amount of moisture of the skin. The information on the amount of moisture of the skin may be set and input from a user using the input apparatus 40 or may be acquired from information output from an apparatus that measures the amount of moisture of the skin. As the apparatus that measures the amount of moisture of the skin, a known apparatus may be used.

Alternatively, a table in which information on a peeling state of stratum corneum and dryness of the skin are associated with each other may be stored in the data server apparatus 50, and the shape information acquisition unit 22 may acquire information on the peeling state of the stratum corneum with reference to the table on the basis of information on input dryness of the skin. The information on the dryness of the skin may be set and input using the input apparatus 40, or may be acquired from information output from the apparatus that measures the dryness of the skin. Further, the dryness of the skin may be acquired on the basis of the image captured by the microscope. Specifically, similar to the above-described embodiment, a brightness image may be generated from an image captured by a microscope, and the area or an area ratio of a white portion of the brightness image may be acquired as the information on the dryness of the skin.

In addition, in the above-described embodiment, the shape information acquisition unit 22 acquires information on sulci cutis of the skin on the basis of an image of the surface of the skin captured by the microscope, but the invention is not limited thereto. For example, information on sulci cutis may be acquired by performing three-dimensional measurement of sulci cutis of the skin using a confocal microscope or the like. In the above-described embodiment, information on a tilt angle of sulci cutis of the skin is acquired on the basis of information on the width of the sulci cutis and a minimum brightness value, but it is possible to acquire information on a more accurate depth of the sulci cutis by performing the three-dimensional measurement as described above, and to acquire information on a more accurate tilt angle. Further, instead of direct measurement of the skin, a silicone is pushed against the skin to take replicas of the skin, and the replicas are three-dimensionally measured to acquire information on sulci cutis.

Furthermore, a configuration in which information on a scattering coefficient within the skin is stored in the data server apparatus 50 shown in FIG. 1 and the optical feature information acquisition unit 23 may read and acquire the information on the scattering coefficient from the data server apparatus 50 on the basis of input predetermined information may be used. Specifically, for example, a table in which information on a scattering coefficient and information indicating the state of melanin in the skin are associated with each other may be stored in the data server apparatus 50 in advance, and the optical feature information acquisition unit 23 may acquire the information on the scattering coefficient with reference to the table on the basis of the information indicating the state of the input melanin. As the information indicating the state of melanin, the amount, the density, and the like of melanin may be used. The information indicating the state of melanin may be set and input from a user using the input apparatus 40 or may be acquired from information output from an apparatus that measures melanin in the skin. As an apparatus that measures melanin in the skin, a known apparatus may be used.

Alternatively, a table in which information on a scattering coefficient and age information of a person who is an evaluation target are associated with each other may be stored in the data server apparatus 50 in advance, and the optical feature information acquisition unit 23 may acquire information on the scattering coefficient with reference to the table on the basis of the input age information. The table in which the information on the scattering coefficient and the age information are associated with each other may be created by measuring scattering coefficients of samples of various ages.

EXPLANATION OF REFERENCES

1: skin evaluation system
10: imaging apparatus
20: skin evaluation apparatus
21: skin image acquisition unit
22: shape information acquisition unit
23: optical feature information acquisition unit
24: evaluation unit
25: display control unit
30: display apparatus
40: input apparatus
50: data server apparatus

What is claimed is:
1. A skin evaluation apparatus comprising
a processor configured to:
acquire information indicating a state of a stratum corneum of a skin, a width of a sulci cutis of the skin, a tilt angle of the sulci cutis of the skin, and a density of the sulci cutis of the skin, as information on a surface unevenness shape of the skin;
acquire a scattering coefficient within the skin, as information on an optical feature of the skin; and
evaluate gloss of the skin on the basis of the information on the surface unevenness shape of the skin and the information on the optical feature of the skin.
2. The skin evaluation apparatus according to claim 1,
wherein the processor acquires an image obtained by imaging the skin and acquires the information on the surface unevenness shape of the skin on the basis of the acquired image.
3. The skin evaluation apparatus according to claim 2,
wherein the processor evaluates that the gloss of the skin is good in a case where a ratio of an area of a peeling portion of the stratum corneum to an area of the acquired image is 20% or less, the width of the sulci cutis of the skin is within 50±30 µm, the tilt angle of the sulci cutis of the skin is 80 degrees or greater and 90 degrees or smaller, and a ratio of an area of the sulci cutis of the skin to the area of the acquired image is 30% or greater.
4. The skin evaluation apparatus according to claim 1,
wherein the processor acquires an image obtained by imaging peeling of the stratum corneum taken from the skin and acquires the information on the surface unevenness shape of the skin on the basis of the acquired image.
5. The skin evaluation apparatus according to claim 1,
wherein the processor reads and acquires the information on the surface unevenness shape of the skin which is stored in a data server apparatus.
6. The skin evaluation apparatus according to claim 1,
wherein the processor acquires a slit optical image captured by irradiating the skin with slit light and acquires the scattering coefficient within the skin on the basis of the slit optical image.
7. A skin evaluation method comprising:
acquiring information indicating a state of a stratum corneum of a skin, a width of a sulci cutis of the skin, a tilt angle of the sulci cutis of the skin, and a density of the sulci cutis of the skin, as information on a surface unevenness shape of the skin;
acquiring a scattering coefficient within the skin, as information on an optical feature of the skin; and
evaluating gloss of the skin on the basis of the information on the surface unevenness shape of the skin and the information on the optical feature of the skin.
8. A non-transitory computer readable recording medium storing a skin evaluation program that, when executed, causes a computer to:
acquire information indicating a state of a stratum corneum of a skin, a width of a sulci cutis of the skin, a tilt angle of the sulci cutis of the skin, and a density of the sulci cutis of the skin, as information on a surface unevenness shape of the skin;
acquire a scattering coefficient within the skin, as information on an optical feature of the skin; and
evaluate gloss of the skin on the basis of the information on the surface unevenness shape of the skin and the information on the optical feature of the skin.

* * * * *